United States Patent [19]
van den Berg

[11] Patent Number: 5,823,134
[45] Date of Patent: Oct. 20, 1998

[54] MILK SAMPLING DEVICE AND METHOD

[75] Inventor: Karel van den Berg, Bleskensgraaf, Netherlands

[73] Assignee: Maasland N.V., Netherlands

[21] Appl. No.: 665,726

[22] Filed: Jun. 18, 1996

[30] Foreign Application Priority Data

Jun. 21, 1995 [NL] Netherlands ............................ 1000620
Oct. 19, 1995 [NL] Netherlands ............................ 1001448

[51] Int. Cl.⁶ ................................................ A01J 5/017
[52] U.S. Cl. ................................ 119/14.02; 119/14.08; 141/275
[58] Field of Search ............................ 119/14.08, 14.18, 119/14.46, 14.02, 14.01; 141/1, 270, 275, 276, 284

[56] References Cited

U.S. PATENT DOCUMENTS

| | | | |
|---|---|---|---|
| 3,168,124 | 2/1965 | Lenkey ..................................... | 141/284 |
| 3,570,555 | 3/1971 | Gilson ......................................... | 141/1 |
| 3,623,381 | 11/1971 | Crepin ....................................... | 74/822 |
| 5,431,128 | 7/1995 | Nilsson et al. ........................ | 119/14.08 |

FOREIGN PATENT DOCUMENTS 0 564 023 A1  10/1993  European Pat. Off. .
2154991  5/1993  France .
1264201  2/1992  United Kingdom .

OTHER PUBLICATIONS

European Search Report for European Patent Application No. EP 96 20 1327.

*Primary Examiner*—Christopher A. Bennett
*Attorney, Agent, or Firm*—Penrose Lucas Albright

[57] ABSTRACT

A milk sampling device is provided with a removable cassette in which milk sample collecting elements can be placed, and at least one filling member capable of being placed successively above various collecting elements. Said filling member is capable of introducing milk samples, taken from milk from an automatic milking machine, into the collecting elements. There is provided a guide supporting at least one filling member, which guide is designed so that the filling member is moved, by increasing the distance between the guide and the cassette and by subsequently decreasing said distance, from a position above a collecting element to an adjacent position above an adjacent collecting element. In particular, the milk sampling device is appropriate for an apparatus that automatically connects teat cups to the teats of an animal, automatically milks the animal and thereafter automatically disconnects the teat cups from the animal's teats.

19 Claims, 3 Drawing Sheets

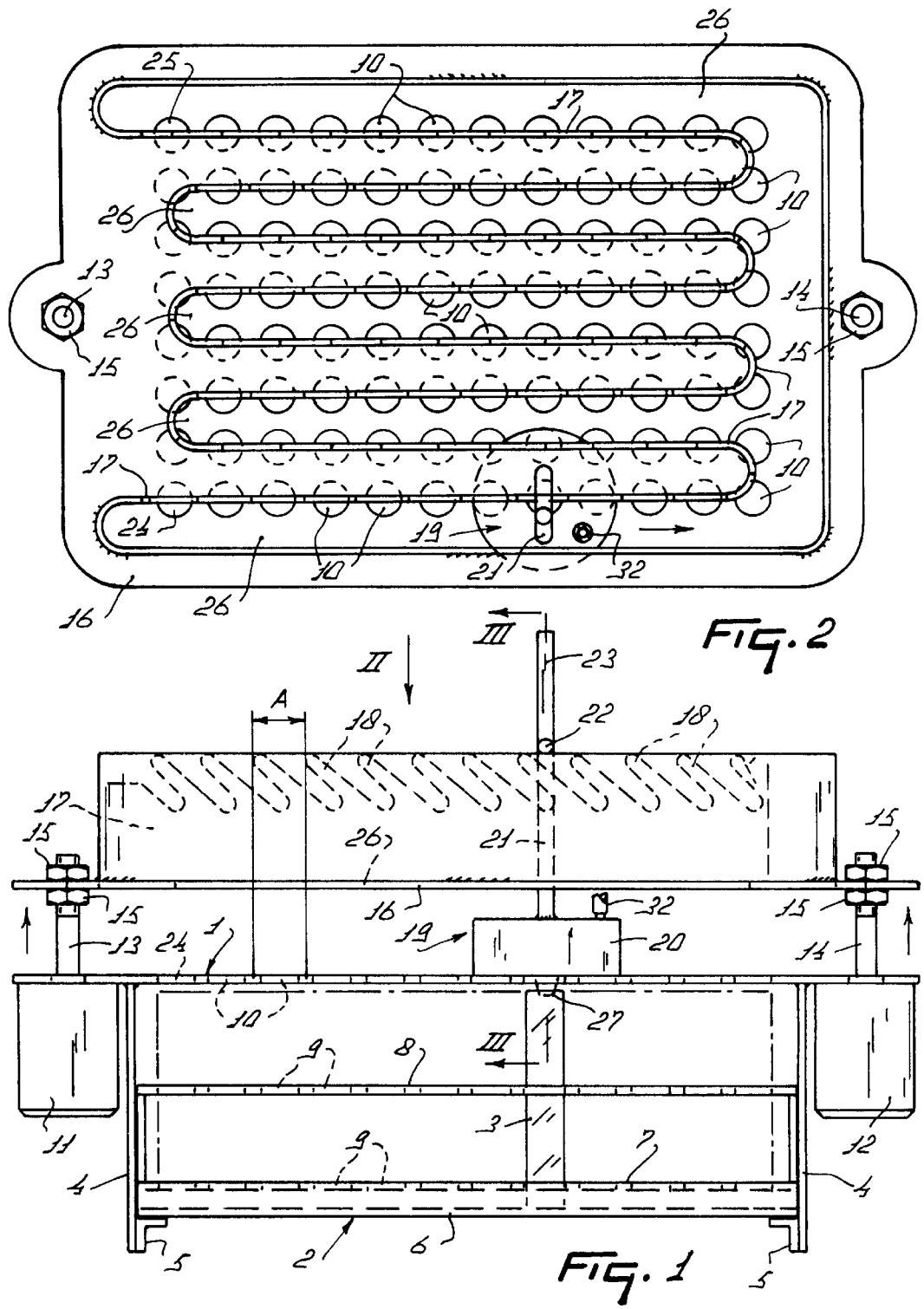

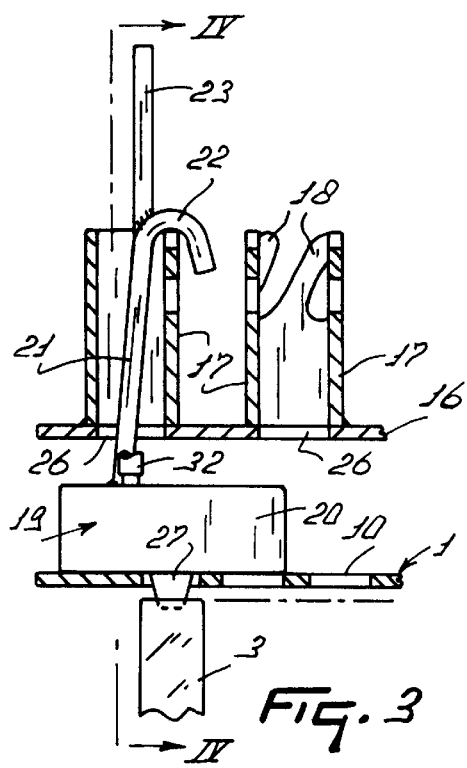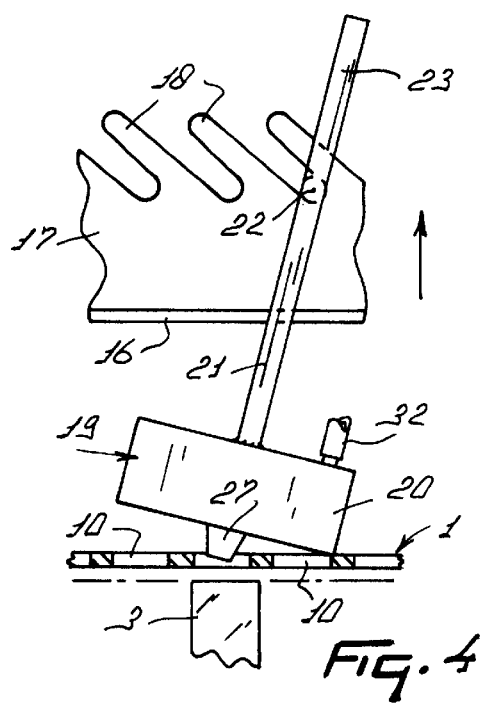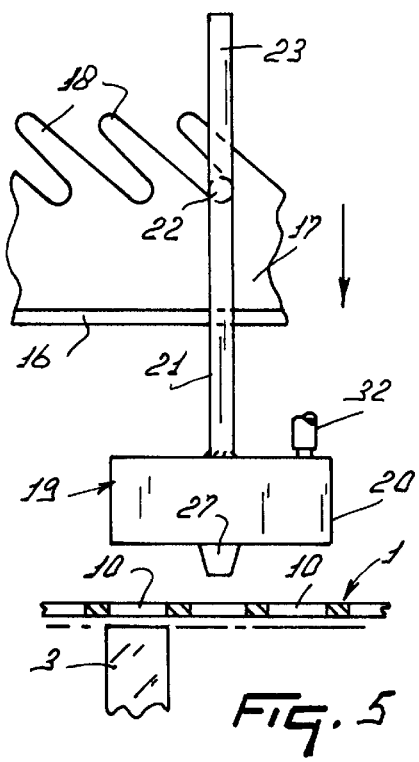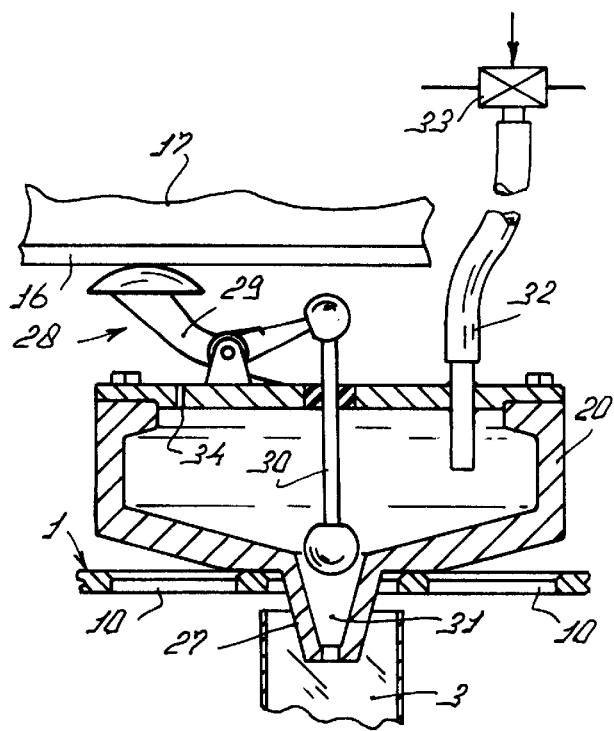

MILK SAMPLING DEVICE AND METHOD

FIELD OF INVENTION

The present invention relates to a milk sampling device, provided with a removable cassette in which milk sample collecting elements can be placed, and at least one filling member capable of being placed successively above various collecting elements, which filling member is capable of transmitting milk samples, taken from milk yielded by means of an automatic milking machine, into the collecting elements.

1. Background of the Invention

A similar milk sampling device is known from EP-A1-0564023. The cassette described in that document is designed as a rotating box in which, along its circumference, the milk sample collecting elements can be arranged. The filling member is disposed in a fixed position, while the collecting elements can be placed successively under the filling member. The filling member is further provided with a vertically movable type of injection needle to be inserted into the collecting elements. In this construction, the cassette and the injection needle have to be moved synchronously. However, in case of a relatively large number of collecting elements, the space in the box is insufficiently utilized. Therefore, the cassette occupies a relatively large space, which, in view of the extensive equipment present in a milking apparatus, is a drawback. Moreover, the synchronous movement of the box and the injection needle complicates control of the units.

2. Summary of the Invention

For the purpose of obviating the aforementioned difficulties or at least attenuating them to a considerable extent, the milk sampling device described in the first paragraph is provided a guide means supporting the filling member, which guide means is designed so that the filling member is moved, by increasing the distance between the guide means and the cassette and by subsequently decreasing said distance, from a position above a collecting element to an adjacent position above a nearby situated collecting element. In particular, the guide means is vertically movable and the cassette is in a fixed position. Such a sampling device has the great advantage that, by only one movement in a vertical direction of the filling member relative to the cassette including collecting elements, the filling member is positioned automatically above a next collecting element.

In a concrete embodiment, the guide means is designed as a substantially vertically disposed strip, on the upper edge of which there are provided tines extending obliquely upwardly and parallel to each other, while the mutual distance of said tines corresponds to that of collecting elements juxtaposed in the cassette. In order to utilize the space in the cassette optimally, the collecting elements can be arranged in the cassette in rows, and the guide means is disposed folded above the collecting elements placed in the cassette in such a way that the filling member is subsequently movable in opposite directions over the rows of collecting elements.

For the purpose of injecting each time a defined quantity of milk into the collecting elements, the filling member comprises a milk sample reservoir capable of being suspended, by means of a suspension element, from the guide means. In order to move the filling member, and in particular the milk sample reservoir, each time above a next collecting element, it will suffice to provide at least one operating cylinder, by means of which the guide means is movable in height relative to the cassette. In particular, there are provided two, preferably computer-controlled, operating cylinders for moving the guide means vertically relative to a support, while the cassette can removably be disposed thereunder. Said support will then be provided with apertures situated above the open ends of the collecting elements placed in the cassette located under the support.

In the filling position, the milk sample reservoir preferably rests on the support, i.e. in a position in which the discharge opening of the milk sample reservoir is situated above the open end of a collecting element or in the upper part thereof, and the suspension element is detached from the guide means. In said filling position, the guide means will take its lowest position relative to the support, in which position, by means of a discharge control member, a milk sample can flow out of the milk sample reservoir, while, upon moving the guide means upwards, the discharge control member will close off the discharge opening of said milk sample reservoir.

As a next collecting element only has to be filled when a next animal is milked and, consequently, taking of milk samples will be coupled with milking of the animals, it is advantageous when the supply of the milk to the milk sample reservoir is entirely controlled by a computer. A milk sampling device of which both the supply of the milk to the milk sample reservoir and the vertical movements of the guide means are computer-controlled may advantageously be applied in an apparatus for automatically connecting teat cups to the teats of an animal, respectively disconnecting same therefrom and for automatically milking the animal. In such a machine connecting and disconnecting of teat cups and milking of the animal being effected without human intervention, the taking of milk samples will have to accomplish in the same manner. In particular when such an apparatus is provided with a milk glass for collecting the milk obtained from the udder quarters of the animal via the teat cups, and a milk tank in which the milk pumped out of the milk glass is stored, the fraction of milk supplied from the milk glass to the milk sampling device will each time be determined by means of a computer.

DESCRIPTION OF THE DRAWINGS

For a better understanding of the invention and to show how the same may be carried into effect, reference will now be made, by way of example, to the accompanying drawings, in which:

FIG. 1 shows schematically a vertical longitudinal cross-section of the milk sampling device according to the invention;

FIG. 2 shows a plan view of said milk sampling device;

FIG. 3 is a partial side view of the milk sampling device;

FIGS. 4 and 5 show the position of the filling member relative to the guide means when the filling member is moved, i.e. upon moving the guide means upwards and downwards;

and FIG. 6 shows a vertical cross-section of the filling member in the filling position.

DESCRIPTION OF THE PREFERRED EMBODIMENT

Figure 7:
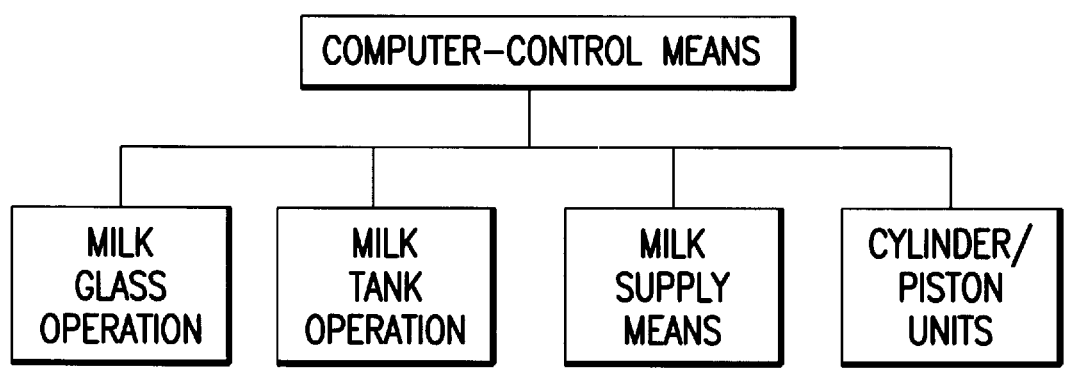
FIG. 7 shows schematically the computer-control means for the piston/cylinder units, the milk supply means, and the milk tank and milk glass operation.

The milk sampling device represented in FIG. 1 comprises a support indicated generally by reference numeral 1, under which a cassette designated generally by reference numeral 2 for milk sample collecting elements 3, which may be vials or test tubes has removably been provided. For that purpose, under support 1 there are fastened side plates 4, which are provided, at their lower sides, with supporting elements 5. The cassette 2 is movable between side plates 4, over supporting elements 5 and can thus be removed from the milk sampling device. In cassette 2, above a bottom plate 6 thereof, there are arranged plates 7 and 8, which are both provided with apertures 9, in which milk sample collecting elements 3 can be accommodated so as to rest on bottom plate 6. Apertures 9 in plates 7 and 8 are arranged in rows, and are in the present embodiment circular so as to correspond with the tubular design of milk sample collecting elements 3 to be arranged in rows in cassette 2. Support 1, under which the cassette 2 has been disposed, is also provided with apertures 10, that have the same size as apertures 9 in plates 7 and 8 or are somewhat smaller. Said apertures 10 are situated above the open ends of milk sample collecting elements 3 placed in the cassette. Under support 1 there are mounted on both sides operating cylinders/piston 11 and 12. The pistons 13 and 14, of each units that are vertically movable in the housing of said operating cylinders, are rigidly connected, by means of bolts 15, to a plate 16 arranged thereabove. On said plate 16 there is vertically provided a guide means 17. The latter is made of strip-shaped material folded in such a way that the strip, once having been arranged vertically on the plate 16, passes all the apertures 10 in support 1. The ends of the strip are welded against each other in such a way that the strip, although being folded in a zigzag fashion, constitutes a closed unit, as is shown in FIG. 2. At the upper edge, the portion of the strip-shaped material constituting the circumference thereof is smooth, whereas the portion of the strip-shaped material folded in a zigzag fashion, that is located therein-side, is provided with tines extending at the upper edge obliquely upwardly and parallel to each other. The mutual distance A of these tines corresponds with the distance between two milk sample collecting elements 3 juxtaposed in the cassette 2.

The milk sampling device is further provided with a filling member designated generally by a reference numeral 19, constituted by a milk sample reservoir 20, and a suspension element 21 attached to the upper side thereof, by means of which the milk sample reservoir 20 can be suspended from the guide means 17. To that end, the suspension element 21 comprises at the upper side a curved or hooked end 22 capable of being received by the upper edge of the guide means 17. See FIG. 3, this bended end 22, there is provided an upwardly projecting portion 23 for the purpose of moving the milk sample reservoir 20 manually, if required, over the guide means 17. This will in particular be the case when the milk sample reservoir 20 has to be brought, from its position above a first milk sampling collecting aperture 24, over the circumferential edge of guide means 17, which circumferential edge is smooth at the upper side, to the position above a last milk sampling collecting aperture 25. At the side of guide means 17 where suspension element 21 of milk sample reservoir 20 is situated, there are provided in plate 16, in longitudinal direction next to the guide means, slot-shaped apertures 26 that together have a comb configuration and are designed in such a way that, as the filling member 19 is moved over the guide means 17, the milk sample reservoir 20 moves underneath plate 16.

In the filling position, milk sample reservoir 20 rests on support 1. In said position, guide means 17 is in its lowest position, while the hook end 22 of suspension element 21 is detached from tines 18, i.e. said hook end is situated just above the horizontal tangent of the tines. At the lower side of the milk sample reservoir 20 there is provided a discharge nozzle 27 which, in the filling position, is inserted through the relevant opening 10 in the support into the upper end of a relevant milk sampling collecting element 3. When, thereafter, operating cylinders/piston 11 and 12 are excited, plate 16 is moved upwards together with the guide means 17. Hook end 22 of the suspension element 21 then moves obliquely downwards in the slot-shaped aperture between two tines 18, while the filling member assumes a tilted position, as is shown in FIG. 4. When, from the latter position shown in FIG. 4, the guide means is moved further upwardly milk sample reservoir 20 together with the discharge nozzle 27 is drawn out of the relevant aperture 10 in support 1 and milk sample reservoir 20, due to its assumes weight, the horizontally suspended position shown in FIG. 5. In the latter position, the discharge nozzle 27 of the milk sample reservoir 20 is located above a next aperture 10 in the support 1. When, from said position, the guide means 17 is moved downwards by means of the operating cylinders/piston unit 11 and 12, while discharge nozzle 27 is already inserted into aperture 10 in support 1, the milk sample reservoir 20 is slightly tilted of position until the hook end 22 is disengaged from the slot between two tines 18 and thus is detached from guide means 17, where upon the milk sample reservoir under the influence of gravity assumes an upright position and, resting on support 1, is again in the filling position, the discharge nozzle 27 being inserted this time into a next aperture. When, upon moving the guide means 17 downwards to its lowest position, i.e. the filling position, the plate 16 contacts a discharge control member 28 (shown in FIG. 6). Said discharge control member 28 comprises a lever beam 29 one end of which, as soon as the filling position is reached by guide means 17 being moved downwards, is tilted downwardly, while the other end is moved upwardly, so that a closing valve member 30 connected to the other end of lever beam 29 opens a discharge opening 31 of milk sample reservoir 20. When guide means 17 moves upwardly, the lever beam 29 is tilted under spring force to a position in which the closing member is moved downwards and discharge opening 31 is closed off. The milk sample reservoir 20 is further connected to a milk supply line 32. In this embodiment, there is provided in said milk supply line 32 a computer-controlled three-way cock 33, by means of which a defined quantity of milk can be supplied to milk sample reservoir 20. For that purpose, first the cock 33 is set in the position in which milk is guided via the milk supply line 32 to the milk sample reservoir 20, and the space in milk sample reservoir 20 is filled during a predetermined time. Said time is selected to provide milk level in the milk sample reservoir is above the outflow of the milk supply line 32 in the milk sample reservoir 20. Then, cock 33 is set in position in which it is connected to a vacuum line of the milk line system, e.g. to a milk glass included in said system, through which milk glass milk is drawn out of the milk sample reservoir until the milk level has dropped so as to have reached the outflow of milk supply line 32 in the milk sample reservoir 20. By providing an air suction opening 34 in the upper surface of the milk sample reservoir 20, the milk level will not drop farther. The quantity of milk in the milk sample reservoir 20 is then accurately defined, which, because of foaming of the milk during filling, would not have been the case if the milk sample reservoir would have been entirely filled at once. In the filling position, by means of discharge control member 28, the quantity of milk thus defined can be admitted to a relevant milk sample collecting element 3 located under milk sample reservoir 20.

Therefore, by means of a computer, not shown on the one hand there is admitted a defined quantity of milk to the milk sample reservoir, while on the other hand the filling member is moved by means of the computer-controlled operating cylinder/piston units 11 and 12 and, upon reaching each new position, will be located above a collecting element.

An above-described milk sampling device may advantageously be used in an entirely automated milking apparatus, i.e. a milking apparatus that operates without human intervention. In an apparatus of this type, the connecting of teat cups to the teats of an animal to be milked, and disconnecting same therefrom as well as the milking proper are effected automatically. During the milking proper, the milk yielded from the udder quarters via the teat cups is usually stored in a milk glass, which milk glass often serves at the same time as a quantity meter, whereafter the milk is pumped from the milk glass to a refrigerated tank for milk storage. From the milk pumped out of a such milk glass there may be taken a fraction to be supplied, via the milk supply line 32, to the milk sampling device. Each time an animal is milked, there can be tapped, in this way, a milk sample from the animal's milk which is supplied to a next milk sampling collecting element.

The foregoing detailed description has been given for clearness of understanding only and no unnecessary limitations should be understood therefrom, for modifications will be obvious to those skilled in the art.

Having disclosed my invention, what I claim as new and to be secured by Letters Patent of the United States is:

1. A milk sampling device which comprises a removable cassette in which a plurality of milk sample collecting elements are received, a filling member capable of being placed successively above various said collecting elements, said filling member connected to receive milk obtained by an automatic milking machine and to introduce said milk into said collecting elements, a guide means supporting said filling member, means for raising and lowering said guide means, said means for raising and lowering said guide means performing the function of raising said guide means whereby said filling member raises from a first said collecting element, moves laterally and lowers so said filling member is above a second said collecting element adjacent said first collecting element in said cassette.

2. A milk sampling device as claimed in claim 1, comprising support means for supporting said filling member in its lowered position, wherein said guide means is vertically movable relative to said support means.

3. A milk sampling device as claimed in claim 2, comprising a cylinder/piston unit interconnecting said support means and said guide means for moving said guide means relative to said cassette.

4. A milk sampling device as claimed in claim 1, wherein said collecting elements are arranged in said cassette in rows, and said guide means has a sinusoidal shape, as seen in plan above said collecting elements, and is constructed and arranged so that said filling member is movable in opposite directions in a sinuous path over said rows of said collecting elements.

5. A milk sampling device as claimed in claim 1, wherein said filling member comprises a milk sample reservoir and a suspension element attached to the upper side of said milk sample reservoir, said milk sample reservoir being suspended from said guide means by said suspension element.

6. A milk sampling device as claimed in claim 1, comprising milk supply means to supply milk to said filling member, said milk supply means being computer-controlled.

7. A milk sampling device as claimed in claim 6, wherein said milk supply means is provided with a computer-controlled three-way cock, by means of which, in a first position, during a predetermined time, milk via said milk supply means is supplied to said filling member, said predetermined time being chosen so that milk is introduced to a level in said filling member above an outflow of milk from said milk supply means into said filling member, whereafter said cock having been set in a second position, milk is drawn out of said filling member until the milk level has descended to the level of said outflow of milk from supply means into said filling member.

8. A milk sampling device as claimed in claim 1, in combination with an apparatus for automatically connecting teat cups to the teats of an animal and disconnecting same therefrom and for automatically milking said animal.

9. A milk sampling device as claimed in claim 8, said apparatus comprising milk glass for collecting milk obtained from udder quarters of said animal via said teat cups, a milk tank in which the milk pumped out of said milk glass is stored, and a computer which causes a fraction of milk from the milk glass to be transmitted to the milk sampling device.

10. A milk sampling device which comprises a removable cassette in which a plurality of milk sample collecting elements are received, a filling member capable of being placed successively above various said collecting elements, said filling member connected to receive milk obtained by an automatic milking machine and to introduce said milk into said collecting elements, a guide means supporting said filling member, said guide means performing the function of raising said filling member from a first said collecting element, moving said filling member laterally and lowering said filling member so it is above a second said collecting element adjacent said first collecting element in said cassette, and wherein said guide means comprises a substantially vertically disposed strip having an upper edge provided with a plurality of tines extending obliquely upwardly and parallel to each other, the distance between adjacent of said tines corresponding to that between adjacent of said collecting elements which are juxtaposed in said cassette.

11. A milk sampling device comprising:
   a removable cassette in which a plurality of milk sample collecting elements are received,
   a filling member capable of being placed successively above various of said collecting elements, said filling member connected to receive milk obtained by an automatic milking machine, and to introduce said milk into said collecting elements,
   a guide means supporting said filling member, said guide means performing the function of raising said filling member from a first said collecting element, moving said filling member laterally and lowering said collecting element so it is above a second said collecting element adjacent said first collecting element in said cassette,
   a support means for supporting said filling member in its lowered position,
   said guide means being vertically movable relative to said support means,
   a cylinder/piston unit interconnecting said support means and said guide means for moving said guide means relative to said cassette, and
   a further cylinder/piston unit similar to said first-mentioned cylinder/piston unit for moving the guide means vertically,
   said support means comprising a support having openings for receiving and aligning said filling member with corresponding said collecting elements, said cassette being removably disposed under said support, said cylinder/piston units arranged to raise and lower said guide means relative to said support.

12. A milk sampling device comprising:

a removable cassette in which a plurality of milk sample collecting elements are received, a filling member capable of being placed successively above various of said collecting elements, said filling member connected to receive milk obtained by an automatic milking machine, and to introduce said milk into said collecting elements, a guide means supporting said filling member, said guide means performing the function of raising said filling member from a first said collecting element, moving said filling member laterally and lowering said collecting element so it is above a second said collecting element adjacent said first collecting element in said cassette, a support means for supporting said filling member in its lowered position, said guide means being vertically movable relative to said support means, said support means comprising a support having openings for receiving and aligning said filling member with corresponding said collecting elements, said cassette being removably disposed under said support, a cylinder/piston unit interconnecting said support means and said guide means for moving said guide means relative to said cassette, a further cylinder/piston unit similar to said first-mentioned cylinder/piston unit for moving the guide means vertically, said cylinder/piston units arranged to raise and lower said guide means relative to said support, and computer-control means for operating said cylinder/piston units.

13. A milk sampling device comprising:

a removable cassette in which a plurality of milk sample collecting elements are received, a filling member capable of being placed successively above various said collecting elements, said filling member connected to receive milk obtained by an automatic milking machine and to introduce said milk into said collecting elements, a support means for supporting said filling member in its lowered position, said cassette being removably disposed under said support means, said support means comprising a support having openings for receiving and aligning said filling member with corresponding said collecting elements, wherein each of said collecting elements comprises an open end, each said open end of said collecting elements in said cassette are aligned with a corresponding opening of said openings in said support, a guide means also supporting said filling member, said guide means being vertically movable relative to said support means, said guide means performing the function of raising said filling member from a first said collecting element, moving said filling member laterally and lowering said filling member so it is above a second said collecting element adjacent said first collecting element in said cassette, a cylinder/piston unit interconnecting said support means and said guide means for moving said guide means relative to said cassette, a further cylinder/piston unit similar to said first-mentioned cylinder/piston unit for moving the guide means vertically, and computer-control means for operating said cylinder/piston units, said cylinder/piston units arranged to raise and lower said guide means relative to said support means.

14. A milk sampling device comprising:

a removable cassette in which a plurality of milk sample collecting elements are received, a filling member capable of being placed successively above various of said collecting elements, said filling member connected to receive milk obtained by an automatic milking machine, and to introduce said milk into said collecting elements, a guide means supporting said filling member, said guide means performing the function of raising said filling member from a first said collecting element, moving said filing member laterally and lowering said collecting element so it is above a second said collecting element adjacent said first collecting element in said cassette, a support means for supporting said filling member in its lowered position, said guide means being vertically movable relative to said support means, and wherein in a filling position, said milk sample reservoir rests on said support means above said cassette and a discharge opening of said milk sample reservoir is situated above an open end of a said collecting element while being detached from said guide means.

15. A milk sampling device comprising:

a removable cassette in which a plurality of milk sample collecting elements are received, a filling member capable of being placed successively above various of said collecting elements, said filling member connected to receive milk obtained by an automatic milking machine, and to introduce said milk into said collecting elements, a guide means supporting said filling member, said guide means performing the function of raising said filling member from a first said collecting element, moving said filling member laterally and lowering said collecting element so it is above a second said collecting element adjacent said first collecting element in said cassette, a support means for supporting said filling member in its lowered position, said guide means being vertically movable relative to said support means, and wherein in a filling position, said milk sample reservoir rests on said support means above said cassette and a discharge opening of said milk sample reservoir is situated above an open end of a said collecting element while being detached from said guide means and said guide means is substantially in its lowest position relative to said support means, said milk sample reservoir being provided with a discharge control member which controls said discharge opening in said milk sample reservoir through which a milk sample can flow out of said milk sample reservoir into a said collecting element thereunder.

16. A milk sampling device comprising:

a removable cassette in which a plurality of milk sample collecting elements are received, a filling member capable of being placed successively above various of said collecting elements, said filling member connected to receive milk obtained by an automatic milking machine, and to introduce said milk into said collecting elements, a guide means supporting said filling member, said side means performing the function of raising said filling member from a first said collecting element, moving said filling member laterally and lowering said collecting element so it is above a second said collecting element adjacent said first collecting element in said cassette, a support means for supporting said filling member in its lowered position, said guide means being vertically movable relative to said support means, and wherein in a filling position, said milk sample reservoir rests on said support means above said cassette and a discharge opening of said milk sample reservoir is situated above an open end of a said collecting element while being detached from said guide means and said guide means is substantially in its lowest position relative to said support means, said milk sample reservoir being provided with a discharge control member which controls said discharge opening in said milk sample reservoir through which a milk sample can flow out of said milk sample reservoir into a said collecting element thereunder and upon said guide means being moved upwardly said discharge control member closes the discharge opening of said milk sample reservoir.

17. A method of sampling milk from animals comprising the steps of: (a) transmitting a predetermined quantity of milk to a milk sample reservoir of a milk sampling device, said quantity of milk being sufficient to overfill said milk sample reservoir; (b) withdrawing by vacuum part of said quantity of milk from said sample reservoir; (c) discharging the remaining milk in said milk sample reservoir into a milk sampling collection means; (d) raising, laterally displacing and lowering said milk sample reservoir so that it is positioned over a further milked sampling collection means; and (e) repeating steps (a) through (c) for a further animal whereby a sample of the further animal's milk is received in a further milk sampling collection means.

18. A method in accordance with claim 17, wherein step (d) is performed by disposing a guiding means over said milk sample reservoir to which said milk sample reservoir is connected and raising and lowering said guide means together with said milk sample reservoir relative to said milk sampling collection means, said guide means also moving said milk sample reservoir laterally from over said first mentioned milk sampling connection means to said further milk sampling collection means.

19. A method in accordance with claim 17, wherein the milk withdrawn in step (b) lowers the level of milk to a selected level in said milk sample reservoir so that a uniform quantity of milk is discharged into said sampling collection means in step (c).

* * * * *